(12) United States Patent
Bischoff et al.

(10) Patent No.: US 10,126,153 B2
(45) Date of Patent: Nov. 13, 2018

(54) PARTICULATE MATTER IMPACT SENSOR

(71) Applicant: Deere & Company, Moline, IL (US)

(72) Inventors: Lutz Bischoff, Nuenschweiler (DE);
Dohn W. Pfeiffer, Bettendorf, IA (US);
James J. Phelan, Bettendorf, IA (US)

(73) Assignee: Deere & Company, Moline, IL (US)

( * ) Notice: Subject to any disclaimer, the term of this patent is extended or adjusted under 35 U.S.C. 154(b) by 143 days.

(21) Appl. No.: 14/794,089

(22) Filed: Jul. 8, 2015

(65) Prior Publication Data

US 2016/0025531 A1 Jan. 28, 2016

Related U.S. Application Data

(60) Provisional application No. 62/027,514, filed on Jul. 22, 2014.

(51) Int. Cl.

| | | |
|---|---|---|
| *G01F 1/30* | (2006.01) | |
| *G01N 33/02* | (2006.01) | |
| *G01L 1/14* | (2006.01) | |
| *G01L 1/16* | (2006.01) | |
| *G01L 5/00* | (2006.01) | |
| *A01D 41/127* | (2006.01) | |

(52) U.S. Cl.
CPC ............... *G01F 1/30* (2013.01); *G01L 1/146* (2013.01); *G01L 1/16* (2013.01); *G01L 5/0052* (2013.01); *G01N 33/025* (2013.01); *A01D 41/1273* (2013.01)

(58) Field of Classification Search
CPC ... G01F 1/30; G01L 1/146; G01L 1/16; G01P 15/00

USPC .................................. 73/12.01, 661, 861.73
See application file for complete search history.

(56) References Cited

U.S. PATENT DOCUMENTS

| 4,490,964 A | 1/1985 | Eldridge et al. | |
|---|---|---|---|
| 6,698,272 B1* | 3/2004 | Almirante | G01K 3/00 374/E3.001 |
| 2004/0161919 A1* | 8/2004 | Cha | H01L 21/76837 438/618 |
| 2006/0253942 A1* | 11/2006 | Barrera | B82Y 15/00 73/661 |
| 2009/0075429 A1* | 3/2009 | Sato | H01L 21/6835 438/118 |
| 2012/0055257 A1 | 3/2012 | Shaw-Klein | |
| 2012/0062245 A1 | 3/2012 | Bao et al. | |
| 2013/0111971 A1* | 5/2013 | Pudas | B82Y 15/00 73/12.01 |

(Continued)

FOREIGN PATENT DOCUMENTS

| EP | 0339142 | 11/1989 |
|---|---|---|
| EP | 0339142 A1 | 11/1989 |
| EP | 0872719 | 10/1998 |

(Continued)

OTHER PUBLICATIONS

European Search Report issued in foreign counterpart application No. 15176406.5, dated May 13, 2016 (12 pages).

(Continued)

*Primary Examiner* — Jewel V Dowtin
(74) *Attorney, Agent, or Firm* — Rathe Lindenbaum LLP

(57) ABSTRACT

A particulate matter impact sensor (301) for sensing impacts of particles (106) comprises a support layer (302); and a sensing media layer (300) disposed in front of the support layer (302).

20 Claims, 5 Drawing Sheets

(56) References Cited

U.S. PATENT DOCUMENTS

2017/0372853 A1* 12/2017 Taniguchi ............ H01H 11/045

FOREIGN PATENT DOCUMENTS

EP       0872719 A1    10/1998
GB       1514274        6/1978
GB       1514274 A     6/1978

OTHER PUBLICATIONS

Partial European Search Report issued in foreign counterpart application No. 15176406, dated Dec. 11, 2015 (6 pages).
Satu Rajala, Jukka Lekkala, PVDF and EMFi Sensor Materials—A Comparative Study, www.elsevier.com/locate/procedia, Sep. 5, 2010.
European Search Report for App 15176406.5 dated Feb. 8, 2017.

* cited by examiner

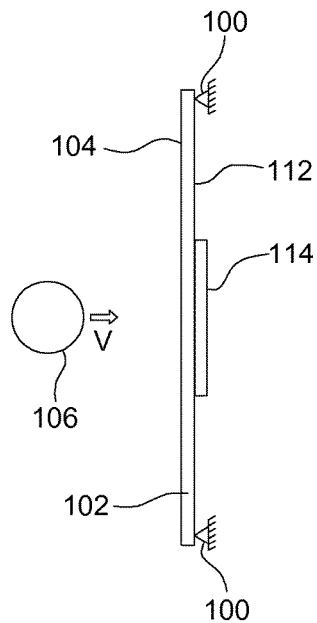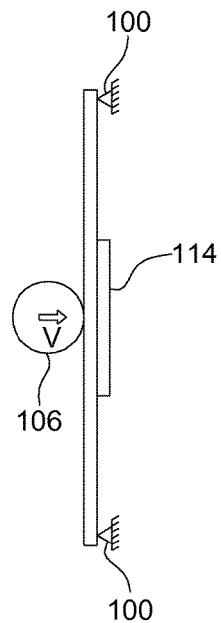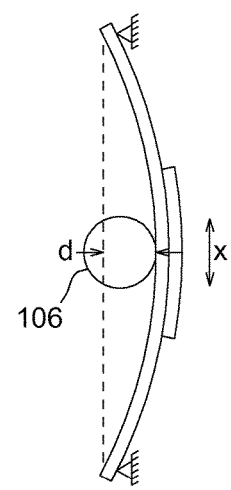
FIG. 3
Prior Art
FIG. 4
Prior Art
FIG. 5
Prior Art
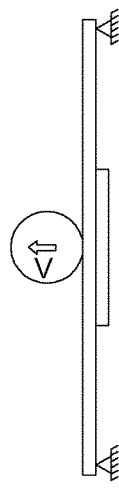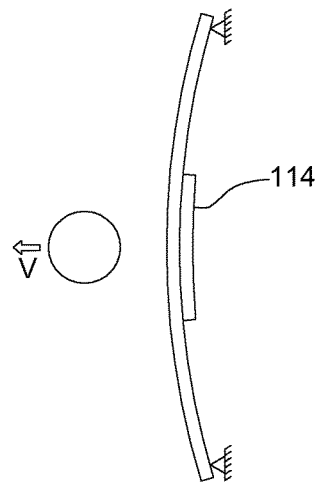
FIG. 6
Prior Art
FIG. 7
Prior Art

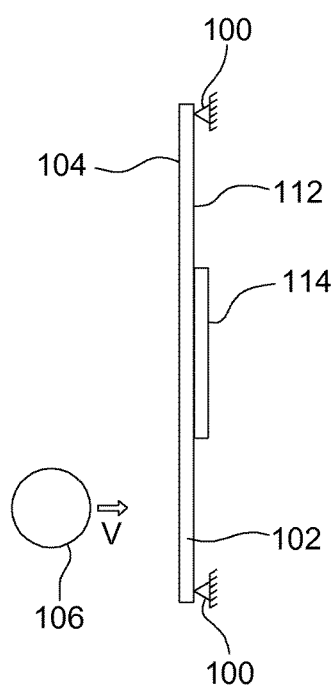
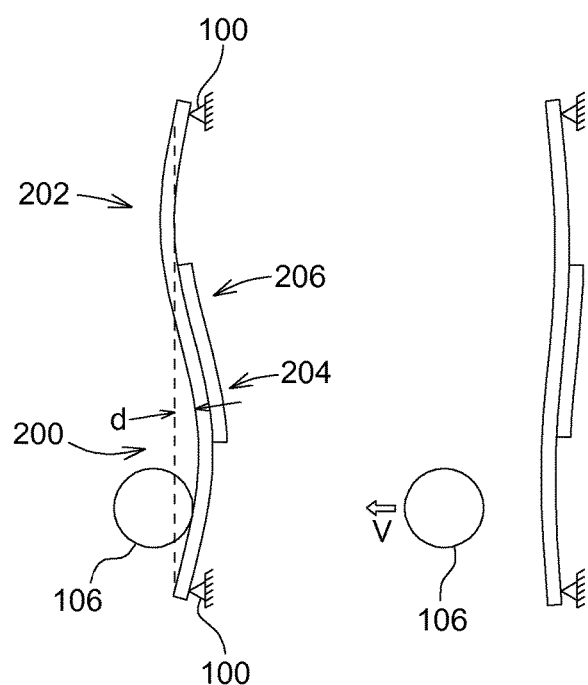
FIG. 8
Prior Art
FIG. 9
Prior Art
FIG. 10
Prior Art

PARTICULATE MATTER IMPACT SENSOR

RELATED APPLICATIONS

This application claims priority to U.S. Provisional Patent Application, Ser. No. 62/027,514, which was filed on Jul. 22, 2014, and entitled "Particulate Matter Impact Sensor".

FIELD OF THE INVENTION

The invention relates to particulate matter impact sensors. More particularly it relates to grain impact sensors for agricultural harvesters.

BACKGROUND OF THE INVENTION

Agricultural harvesters such as combines sever crop plants from the ground, thresh the crop plants, separate the grain portion of the crop plants from the remainder of the crop plants, deposit the remainder of the crop plants (MOG) on the ground, and store the grain in a grain reservoir or tank. Periodically, the grain in the grain reservoir is offloaded to a cart or truck that travels alongside the agricultural harvester and is carried away for storage.

There are several mechanisms inside the agricultural harvester that are used to separate the grain from the MOG. To ensure their proper settings and operation, the performance of various subsystems must be monitored. One way of monitoring the performance of these agricultural harvester subsystems is by determining how much grain passes through particular mechanisms within the agricultural harvester.

One way of monitoring the passage of grain is by use of a particulate matter impact sensor. These impact sensors are typically called "grain sensors" or "grain loss sensors". These types of sensors are configured to sense the impact of a falling kernel of grain upon a surface of the sensor, and to convert this impact into an electrical signal. This raw electrical signal is then processed and transmitted to an ECU for further use.

This use can be as simple as displaying the amount (or relative amount) of grain impacting the sensor. With this information alone, an operator, based on his experience, can adjust the machine manually to improve performance. Alternatively, the use can be more complex, such as by employing the signal to automatically adjust the operating settings of various internal mechanisms of the agricultural harvester.

A common grain loss sensor design in agricultural harvesters comprises a flat impact plate, generally rectangular, to which a sensing element is attached on the rear side of the impact plate. The grain impacts the front side of the impact plate, causing the impact plate to flex.

A sensing element (typically a piezoelectric sensing element in the form of a thin layer) is attached to the back side of the plate. When the plate flexes, it causes the sensing element on the backside the plate to flex in a similar manner. The sensing element, in turn, is coupled to sensing circuits that receive the minute electrical signals from these flexures. The sensing circuits amplify and filter these signals, and convert them into a form that is usable by a digital microprocessor.

The common grain loss sensor design suffers from several defects. Some of these defects are due to the characteristics of the piezoelectric sensing element itself, and some of them are due to the inhomogeneity of the design overall.

Piezoelectric sensing elements mounted as described above, generate minute electrical signals based upon the gross bending of the sensor element rather than the localized bending at the point of impact of the kernel of grain upon the impact plate. The impact plate is typically made of relatively rigid material, such as fiber reinforced plastic, aluminum, or steel that is a few millimeters thick. The kernels of grain contact perhaps a 10 mm$^2$ area of the impact plate. The impact plate, due to its stiffness, however, does not flex locally in response to the impact. Instead, each grain impact causes substantially the entire impact plate to bend inwardly an infinitesimal distance causing an extremely small curvature of the impact plate.

One example of a prior art arrangement can be seen in FIGS. 1-2, the dynamic response of which is discussed below.

In FIG. 1, a shallow metal housing or box 100 is fixed to an impact plate 102. The impact plate 102 has an outer surface 104 against which grains of crop, such as soybeans 106, corn kernels 108, and wheat 110 impact. It has an inside surface 112 which is bonded to a piezoelectric sensing element 114. A signal conditioning circuit 116 is fixed to the sensing element 114. A signal lead 118 is fixed to the signal conditioning circuit to provide it with electrical power and to receive back conditioned signals. These signals are received by an ECU/DSP for further processing and use.

The impact plate 102 is fixed at its edges to the edges of the shallow metal housing 100. It may be fixed with mechanical fasteners 120 such as rivets, bolts, screws, etc., or an adhesive 122. The edges of the impact plate 102 are therefore constrained in their movement by being fixed and/or coupled to the edges of the shallow metal housing 100.

The impact plate 102 is homogeneous in construction in that it has a constant thickness and constant material characteristics over substantially its entire extent.

The impact plate 102 is large compared to the size of the seeds that contact it. The impact plate 102 typically ranges from 75 mm×75 mm to 125 mm×250 mm.

The sensing element 114 does not extend over the entire inner surface of the impact plate 102. Grain can contact the impact plate 102 at any of locations 124, for example, that is disposed away from the sensing element 114. In order to communicate this impact to the sensing element 114 itself, the entire impact plate 102 must flex in response.

To illustrate this effect, an exaggerated view of this flexure in response is shown in FIGS. 3-5.

In FIG. 3, the seed 106 is approaching the impact plate 102 at a velocity "V". The seed approaches the impact plate 102 at the center of the plate, equidistant from all the edges of the plate. The impact plate 102 has the sensing element 114 attached to its inner surface 112. The edges of the housing 100 that support the edges of the impact plate 102 are shown schematically as ground symbols. They are fixed and stationary.

In FIG. 4, the seed 106 has just contacted the impact plate 102. Given the deformation of the typical seed at a velocity "V", the contact area is approximately 2 mm×2 mm.

In FIG. 5, the seed 106 has transferred all of its kinetic energy into the impact plate 102 and has slowed to a stop. The impact plate 102 has stored the kinetic energy of the seed 106 by elastic deformation. The impact plate 102 has flexed inward, becoming concave on its outer surface 104 and convex on its inner surface 112.

In FIG. 5, the impact plate 102 has flexed inward an amount "D". This inward flexure of the impact plate 102 has caused the corresponding and substantially equal flexure of the sensing element 114. Since the sensing element 114 is disposed on the back of the impact plate 102, it is stretched in a direction "X" that is generally parallel to the plane of the sensing element 114. It is also flexed into a similar concave shape as the impact plate 102 since it is bonded to the inner surface 112 of the impact plate 102. This stretching and flexure of the sensing element 114 affects substantially the entire area of the sensing element 114.

In FIG. 6, the energy stored in the impact plate 102 and the sensing element 114 has been released and the seed 106 has been propelled in the reverse direction. The impact plate 102 has returned to its initial position (in this case, generally flat) as well as the sensing element 114. The electrical signal that was produced by the flexure of the sensing element 114 has disappeared since the sensing element 114 has returned to its initial, and stressed, shape.

In FIG. 7, the impact plate 102 and the sensing element 114 continues moving in the reverse direction until both have achieved a convex configuration. In order to get a fast response, the loss sensors are underdamped, which permits them to oscillate convex>concave>convex>concave as the energy input by the seed 106 dissipates. As this oscillation occurs, the signal from the sensing element 114 continues. This "ringing" of the sensor occurs at a relatively low natural frequency, often taking 10 or 15 ms to decay. In an overdamped sensor arrangement, the seed 106 would bounce off the (concave) outer surface 104 (FIG. 5) and the impact plate 102 and the sensing element 114 would gradually return to their planar position (as shown in FIG. 6) without achieving the convex position shown in FIG. 7. In this situation, the gradual restitution of the sensing element 114 to its initial planar shape would cause a gradual falloff of the signal produced by the sensing element 114. As in the case of the underdamped system, this gradual signal falloff can take 5 to 10 ms.

The 5 to 10 ms decay of the signal from the sensing element 114 has been determined to be a function of its overall size, mass, and stiffness.

The description above illustrates the ideal situation in which a seed 106 impacts the center of the impact plate 102 causing equal deflection of the impact plate 102 and the sensing element 114 in all directions. Given the symmetry in all directions about the center contact point of the seed 106 against the impact plate, the physical characteristics of the impact plate 102 and the sensing element 114 mandate that the response will be generally as shown in FIGS. 3-7.

In the real world, however, substantially the entire outer surface 104 of the impact plate 102 can be impacted by the seed 106. When an off-center impact by the seed 106 occurs, the characteristics of the resultant signal changes in unpredictable ways. An off-center impact of the seed 106 against the impact plate 102 is illustrated in FIGS. 8-10.

In FIG. 8, for example, a seed 106 approaches the impact plate 102 in a position that is off-center and adjacent to the edge of the impact plate 102. The impact plate 102 is supported on all sides by the housing 100. As in the examples of FIGS. 3-7, the housing 100 is represented as a ground symbol for convenience of illustration.

In FIG. 9, the seed 106 has contacted the impact plate 102 and has deflected it inward in the region surrounding the point of impact. Since the point of impact is off-center and immediately adjacent to the housing 100 which supports the impact plate 102, the movement of the impact plate is constrained. The impact plate 102 can no longer flex symmetrically across substantially its entire surface. Instead, as the energy of the seed 108 is absorbed by the impact plate 102, the impact plate 102 is deflected into a second mode of oscillation in which a portion 200 of the plate adjacent to the seed 106 is flexed into a concave shape, and a portion 202 of the impact plate 102 away from the seed 106 is flexed into a convex shape. Similarly, the sensing element 114, which is disposed in a center region of the impact plate 102, reproduces a similar convex/concave flexure.

The distance "D" of the concave flexure is smaller than the distance "D" of the concave flexure for a center impact (see FIG. 5) since the seed one impacted the impact plate 102 adjacent to fixed support (i.e. the edge of the impact plate 102 where it is fixed rigidly to the shallow housing 100). Since the distance "D" is reduced for a seed impact adjacent to an edge of the impact plate 102 as compared to a seed impact in the center of the impact plate 102, the sensing element 114 flexes much less, and therefore generates a much smaller electrical signal for impacts adjacent to the edge. This change in signal amplitude based upon the position of the seed impact on the surface of the impact plate 102 makes it difficult to properly condition the signal.

The signal problem is further complicated since the sensing element generates a signal related to its degree of stretching and its flexure. The portion 204 of the sensing element 114 adjacent to the seed and is under tension—it is stretched. However, the portion 206 of the sensing element 114 on the other side of the grain loss sensor is compressed. The signal produced by the sensing element 114 is an average of the tension/compression effects across the entire surface area of the sensing element 114. Since the sensing element 114 is experiencing both a tension in one portion 204 and a compression in another portion 206, the electrical signal generated by the sensing element 114 overall is even further reduced, since these two areas generate opposing electrical signals that (in effect) cancel each other out.

FIG. 10 illustrates the oscillation of the impact plate 102 when the impact plate 102 plus sensing element 114 combination is underdamped after the seed 106 is released. In a typical grain loss sensor of this design, the impact plate 102 can oscillate back-and-forth between the two extreme positions illustrated in FIG. 10. In this case, the impact plate 102 plus sensing element 114 will gradually return to the position shown in FIG. 8 as their energy is dissipated. This can take 5 to 10 ms.

Alternatively, if the impact plate 102 plus sensing element 114 combination is overdamped, it will release the seed 106 in the position shown in FIG. 9 and relax to the generally planar position shown in FIG. 8. Depending on the degree of over damping, this gradual return to the position shown in FIG. 9 can take 5 to 10 ms.

A further complication is the difference in vibrational frequencies generated by the seed one impact of FIGS. 3-7 and the seed 106 impact of FIGS. 8-10. When the impact plate 102 oscillates in its primary mode (shown in FIGS. 3-7) it has a frequency of oscillation that is less than the frequency of oscillation caused by the off-center seed impact shown in FIGS. 8-10. This also adds to the complexity and difficulty of determining individual seed impacts.

In the description above regarding FIGS. 3-10, I have illustrated only two different positions at which the seed 106 may impact the impact plate 102. There are an infinite number of positions at which a seed one can impact the impact plate 102. Further, the wave equation predicts that there are an infinite number of modes of oscillation that can be generated by each impact, each mode of oscillation having its own distinct (and different) frequency and its own distinct (and different) amplitude.

The final complication in determining seed impacts on a grain loss sensor of this design is when several seeds make contact the impact plate at many different locations on the impact plate within milliseconds of each other. Given the long decay time from a single seed impact (5-10 ms), it is virtually impossible to distinguish individual seed impacts when they are occurring faster than once every 20-30 ms or so. There are so many possible modes of oscillation (based upon the location of the strike), there are so many possible amplitudes (based upon the location of the strike) and there is such a long decay time (because of the large mass of the sensing element 114 and the impact plate 102) that identifying and quantifying grain strikes with any accuracy is virtually impossible.

One potential solution is to provide many more of these grain loss sensors and arranging them side-by-side, each of these grain loss sensors having a smaller impact plate. The costs of doing this are high, however.

Another potential solution is to have a single large impact plate 102, but to bond multiple, smaller sensing elements 114 in an array on the back of the impact plate 102. This, too, would be quite costly. The number of electrical interconnections that would have to be made to each individual sensor would be prohibitive. Further, each sensor would still generate a signal that was a composite of the effects of grain strikes all over the sensor plate since the oscillations of the impact plate 102 would still be communicated through the impact plate from the point of impact to other adjacent regions of the impact plate 102. Separating out spurious components of the signal from one sensing element 114 due to grain strikes on a distant portion of the impact plate 102 would be virtually impossible. Finally, as the number of the sensing elements 114 bonded to the back of the impact plate 102 is increased, the size of each sensing element 114 would have to be correspondingly reduced. The reduced size of each sensing element 114 would cause a corresponding reduction in signal amplitude which would thus make each sensing element 114 much less sensitive and much more subject to electrical and mechanical noise.

What is needed, therefore, is a sensor arrangement that is faster, that has less noise, that has a higher frequency of response, and/or has a lower dynamic mass. It is an object of this invention to provide such a sensor arrangement.

SUMMARY OF THE INVENTION

In accordance with one aspect of the invention, a particulate matter impact sensor for sensing impacts of particles is provided that comprises a support layer; and a sensing media layer disposed in front of the support layer.

The sensing media layer may comprise a sheet with cellular voids.

The sensing media layer may comprise an impact responsive layer having an outer surface facing a direction of material flow and an inner surface facing the support layer.

The sensing media layer may have a thickness of no greater than 500 µm.

The sensing media layer may be comprised of biaxially stretched polypropylene.

The particulate matter impact sensor may further comprise a protective layer that is fixed to the sensing media layer and is located between the particles impacting the particulate matter impact sensor and the sensing media layer.

The protective layer may comprise plastic or metal.

The protective layer may comprise a plastic laminate.

The plastic laminate may comprise a fiber reinforced plastic.

The fiber reinforced plastic may comprise glass fibers or carbon fibers.

The protective layer may comprise aluminum.

BRIEF DESCRIPTION OF THE DRAWINGS

FIGS. 1-10 disclose a prior art particulate matter impact sensor.

DETAILED DESCRIPTION OF THE PREFERRED EMBODIMENTS

This new sensor arrangement embodies several inventions and has several different embodiments.

Figure 1:
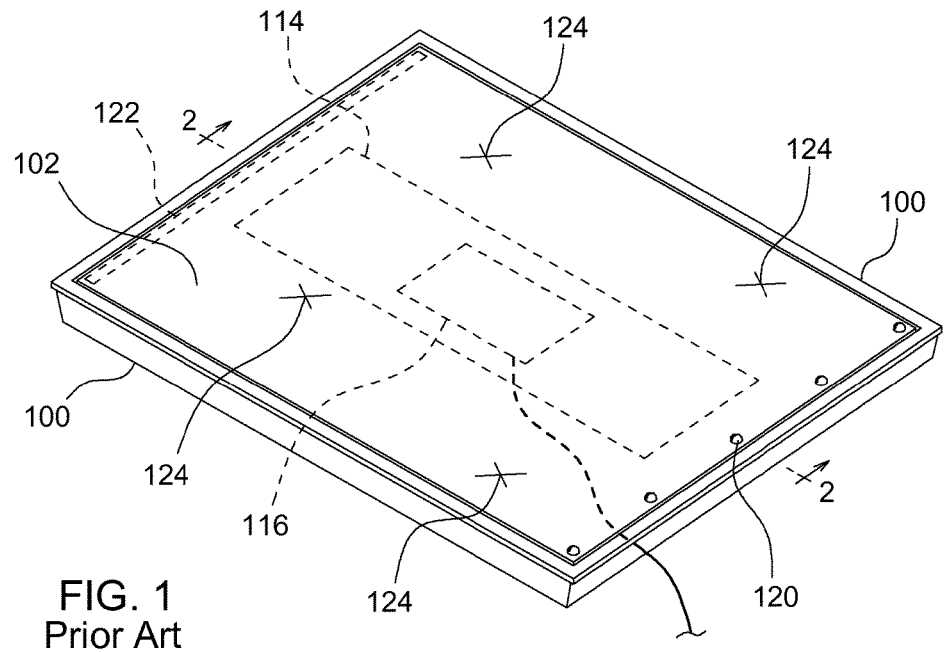
Figure 2:
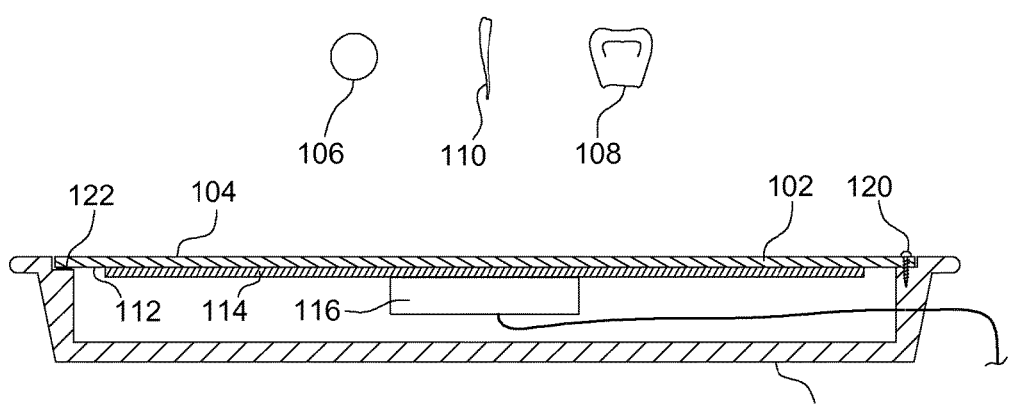
Figure 11:
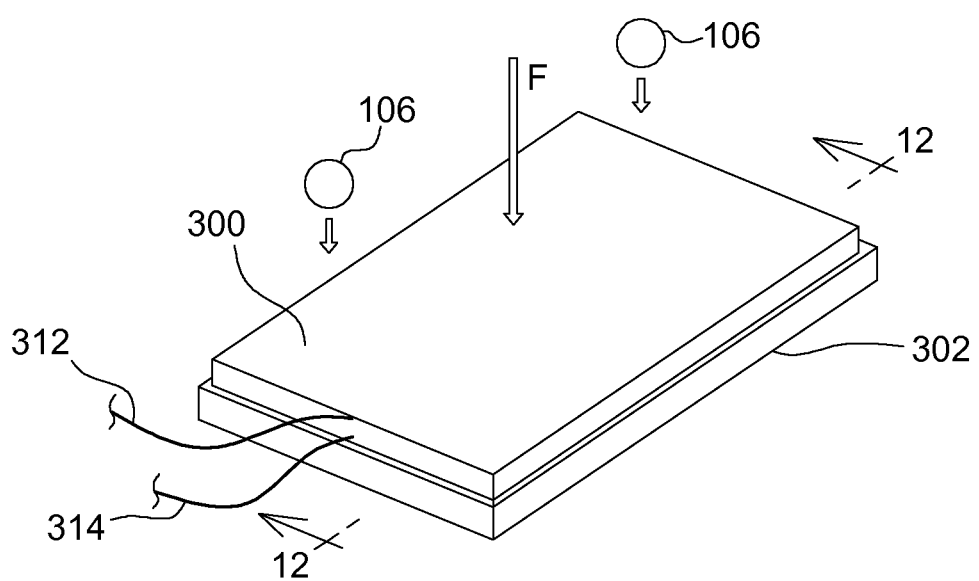
FIGS. 11-14 illustrate a particulate matter impact sensor in accordance with the present invention.

FIG. 11 illustrates a first configuration of a particulate matter impact sensor 301 (e.g. a grain loss sensor). In this arrangement, a sensing media layer 300 is bonded to a support layer 302. The sensing media layer 300 has a first surface 304 that faces the direction of grain flow "F". The sensing media layer 300 has a second surface 306 on the opposite side of the sensing media layer that faces away from the direction of grain flow "F". The second surface 306 is bonded to a first surface 308 of the support layer 302. The first surface 308 of the support layer 302 faces the direction of grain flow "F". The support layer 302 has a second surface 310 that faces away from the direction of grain flow "F".

The sensing media layer 300 is responsive to impacts by seeds 106 traveling in the direction "F" of grain flow. In response to the impacts by seeds 106, the sensing media layer 300 produces an electrical signal at one or more electrical connections 312, 314. The electrical connections 312, 314 are electrically coupled to the sensing media layer 300.

The function of the support layer 302 is to support the sensing media layer 300. A fastening means is used to attach the support layer 302 to the sensing media layer 300. In one arrangement, the fastening means comprises an adhesive disposed between the second surface 306 to the first surface 308. In another arrangement the fastening means comprises a frame extending about the periphery of the sensing media layer. In another arrangement, the fastening means comprises a plurality of spaced up mechanical fasteners such as screws, rivets, bolts, nuts, and clips that extend between and/or through the support layer 302 and the sensing media layer 300. In another arrangement, the support layer 302 and the sensing media layer 300 are formed integral with each other.

Figure 12:
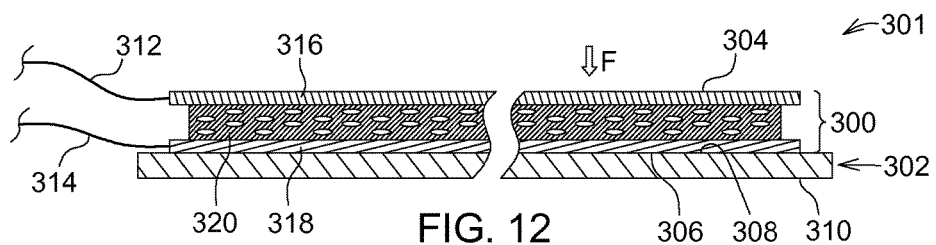

FIG. 12 illustrates a first configuration of the sensing media layer 300. In this arrangement, the sensing media layer 300 has an upper conductive layer 316, a lower conductive layer 318, and an impact responsive layer 320.

The upper conductive layer 316 conducts electricity to or from one surface of the impact responsive layer 320 to the electrical connection 314.

The lower conductive layer 318 conducts electricity to or from an opposing surface of the impact responsive layer 320 to the electrical connection 312.

The impact responsive layer 320 comprises a pressure responsive media that changes its electrical characteristics upon the impact of the seed 106. The electrical characteristics may comprise a change in resistivity, a change in capacitance, or a production of electricity caused by the impact of the seed 106. These electrical characteristics are changed locally in the impact responsive layer 320 immediately adjacent to the location of the seed impact. Typical pressure responsive media includes such things as electromechanical films, cellular polymers, polymer electrets, piezoelectric polymers, piezoelectric films, and quasi-piezoelectric films.

In one particular arrangement the impact responsive layer 320 comprises a cellular polymer sensing media. This material is formed as a thin polypropylene sheet having a cellular structure. This material is manufactured by stretching a polypropylene preform in longitudinal and transverse directions. The stretched sheet is then charged by a corona discharge method. The stretched sheet is full tiny gas voids or "cells" extending in a longitudinal and transverse direction. These cells are separated from one another by leaf-like polypropylene layers. The cells can be compared to large electrical dipoles that are easily compressed in a thickness direction by an externally applied force. The change in thickness at the site of the compression (in our case, the impact site of the seed 106) modifies the dimensions of the dipoles which generates a corresponding electrical charge.

The biaxial stretching and cellular nature of the material causes the cellular polymer media to respond to compression of the media in a direction normal to the planar extent of the media. Advantageously, it also causes the media to be relatively nonresponsive to shear forces applied to the surface of the media. In fact, cellular polymer sensing media can have a 100-fold reduced sensitivity to shearing forces (i.e. sliding contact) as opposed to normal forces (i.e. particle impacts normal to the surface of the media).

This is of particular benefit for grain loss sensors that are disposed normal to a path of incoming, falling grain or other particulate matter. Grain (or other particulate matter) impacting the surface of the sensor normal to the longitudinal and transverse extent of the impact responsive layer will generate a strong signal upon initial (normal) impact. As those same particles slide down the face of the sensor after impact, the shear forces generated by the sliding of the particles will generate a corresponding electric charge which is greatly reduced. This will innately reduce or eliminate the signals generated from second impacts and sliding movement of the particulate matter after the initial impact. In this manner, double (or triple) counts of each seed impact can be reduced or eliminated and therefore the number of particles contacting the sensor can be more accurately counted.

In another arrangement, the impact responsive layer 320 comprises a polar piezoelectric polymer (e.g. polyvinylidenefluoride or PVDF) that generates an electrical charge upon impact.

In another arrangement the impact responsive layer 320 comprises a material that changes its electrical resistance upon impact and compression, such as molybdenum disulfide-based inks, or conductive coating products such as the "Cho-Shield" line produced by Parker-Chomerics of Woburn, Mass.

In another arrangement, the impact responsive layer 320 comprises polymer composites that further comprise polymers (e.g. polymers with polarizable moieties such as polyimides, polyamides, silicon-based polymers, vinyl polymers, polyurethanes, polyureas, polythioureas, polyacrylates, polyesters and/or biopolymers) to which carbon nanotubes (e.g. single wall nanotubes and multiwall nanotubes) have been added, or to which electroceramic particles (e.g. lead-zirconium titanate, lanthanum-modified lead-zirconate titanate, niobium-modified lead-zirconate titanate and/or barium titanate) or to which both have been added. See, for example, published patent application US 2006/0084752 A1, which is incorporated herein by reference for all that it teaches.

In one arrangement, the upper conductive layer 316 and the lower conductive layer 318 may comprise a film base (e.g. a polyimide (e.g. Kapton), BiPEt (e.g. Mylar, Melinex, Hostaphan), polyester or PTFE (polytetrafluoroethylene) (e.g. Teflon) to which a conductive media (e.g. metals such as aluminum, silver, or gold; or conductive oxides such as indium tin oxide; or carbon such as carbon nanotubes or graphene) is deposited by a sputter-, vapor- or plasma-deposition process (with or without post-deposition annealing or curing). In this arrangement, a surface of the upper conductive layer 316 in the lower conductive layer 318 to which the conductive media is applied is then bonded to the impact responsive layer 320. This arrangement has the benefit of providing an outwardly facing (e.g. the surface facing seeds 106) polymer layer that provides strength, flexibility, and durability, yet covers and protects a more fragile conductive media.

In one arrangement, the upper conductive layer 316 and the lower conductive layer 318 are continuous and homogeneous over substantially the entire surface of the impact responsive layer. This is particularly beneficial when used to detect random impacts of particulate matter. In the present case (i.e. that of a grain impact sensor) the particular matter impacts random locations on the surface of the sensor. Grain falls from the threshing and separating section of a combine in essentially a random pattern over the surface of the grain impact sensor. It is not directed to a particular region of the grain impact sensor. Each particle has its own random and unpredictable velocity and location as it falls into the surface of the grain impact sensor. As a result, there is no way to predict the point of impact of any particle.

To accommodate this virtually infinite number of impact locations, substantially the entire surface of the particulate matter sensor is preferably equally responsive to impacts of particles. Thus, the upper conductive layer 316 and the lower conductive layer 318 preferably do not vary in their conductive characteristics over the entire surface of the grain impact sensor. If grain impact occurs at a random location (X, Y) on grain impact sensor and an identical grain impact occurs at a location even as little as 1 mm away from the location (X, Y), an identical electrical change (e.g. a change in resistivity, capacitance, or electrical charge) should be generated by the impact responsive layer 320 and that identical electrical change should be identically communicated through the upper conductive layer 316 in the lower conductive layer 318 to a signal processing circuit. The conveyance of this identical electrical change through the upper conductive layer 316 and the lower conductive layer 318 is enhanced by the continuous and homogeneous characteristics of the upper conductive layer 316 and the lower conductive layer 318 over substantially the entire surface of the grain impact sensor.

The thickness of the upper conductive layer 316 and the lower conductive layer 318 is generally between 7 and 25 μm.

"Dynamic mass" as used herein refers to the mass of the sensor that is moved in order to cause an electrical change sufficient to indicate a grain impact.

"Dynamic volume" as used herein refers to the volume of the sensor that is moved in order to cause an electrical change sufficient to indicate a grain impact.

The "seed-to-sensor mass ratio" as used herein refers to the mass of a seed making an impact divided by the dynamic mass of the sensor that responds to that impact.

In prior art arrangements (shown in FIGS. 1-10) the impact of a single seed 106 flexes substantially the entire impact plate 102 and piezoelectric sensing element 114 in order to generate an electrical signal. The impact plate 102 and the piezoelectric sensing element 114 can typically have a mass that is 20 to 100 times as great as the seed itself—i.e. a seed-to-sensor mass ratio of 0.05 to 0.01. As the inventors have discovered, and as described above in conjunction with FIGS. 1-10, as the seed-to-sensor mass ratio decreases, the natural frequency of the sensor decreases making it hard to identify individual seed impacts upon the sensor surface. Further, the larger, thinner and more flexible the particulate impact sensor is made, the more modes of vibration are generated in the particulate matter impact sensor, each mode having its own natural frequencies of oscillation, which also makes it difficult to identify an individual seed 106 impact from the signal generated by the particulate matter impact sensor.

Even if the seed 106 is traveling at a relatively high speed when it impacts the impact plate 102, the impact of the seed 106 against the impact plate 102 is substantially damped and dissipated. The kinetic energy of movement of the seed 106 must be converted into a flexure of a much larger mass (the impact plate 102 plus the piezoelectric sensing element 114).

In comparison to this prior art arrangement, the dynamic mass of the particulate matter impact sensor 301 is significantly smaller. The dynamic mass of the particulate matter impact sensor 301 is less than the mass of the particles whose impacts are being sensed by the particulate matter impact sensor 301. A corn seed has a mass of about 1000 mg, a soybean seed has a mass of about 800 mg, a barley seed has a mass of about 75 mg, and wheat seed has a mass of about 60 mg. These seeds 106 are rounded, generally spherical, ovoid, or oblate, and have an overall size of 4 mm to 10 mm.

Depending upon the resilience of the sensing media layer 300 and the size and mass of the seed, a typical seed 106 may impact and deflect and/or compress a small surface area (2 mm$^2$ to 10 mm$^2$) of the sensing media layer 300 to a depth typically ranging between 25 and 250 μm. The depth of this depression depends upon the thickness of the sensing media layer 300, the thickness any protective film layer of that may be provided in front of the sensing media layer 300, and the thickness of any intermediate layer (not shown) that may be disposed between the sensing media layer 300 and the support layer 302. This intermediate layer may comprise an adhesive layer provided to attach the sensing media layer 300 to the support layer 302.

The mass density of the sensing media layer 300 can be approximated as 1.3 g/cm^3.

In one example, assume that the sensing media layer is impacted by the seed 106 and is compressed only slightly, e.g. to a depth of 25 μm, and that this compression occurs over of surface area of 2 mm$^2$, the dynamic mass of the particulate matter impact sensor 301 is approximately 17 μg. Assuming that seed 106 is a corn kernel having a mass of 1 g, this arrangement provides a seed-to-sensor mass ratio of 1 g/17 μg or approximately 60,000.

In another example, assume that the sensing media layer is impacted by the seed 106 and is compressed significantly more, e.g. to a depth of 250 μm over a 10 mm$^2$ surface area. In this case, the dynamic mass of the particulate matter impact sensor 301 is approximately 850 μg. Assuming that seed 106 is a corn kernel having a mass of 1 g, this arrangement provides a seed-to-sensor mass ratio of 1 g/850 μg or approximately 1200.

By way of comparison, the dynamic mass of a traditional grain impact sensor (e.g. the one illustrated in FIGS. 1-10) is 27 g and the dynamic volume is 21 cm$^3$. These estimates are based upon an impact plate 102 made of plastic, having a thickness of 2 mm, a width of 7 cm, and a length of 15 cm.

To provide optimum performance, the particulate matter impact sensor 301 has a seed-to-sensor mass ratio greater than 5, alternatively greater than 50, alternatively greater than 500 and alternatively greater than 5000.

Figure 13:
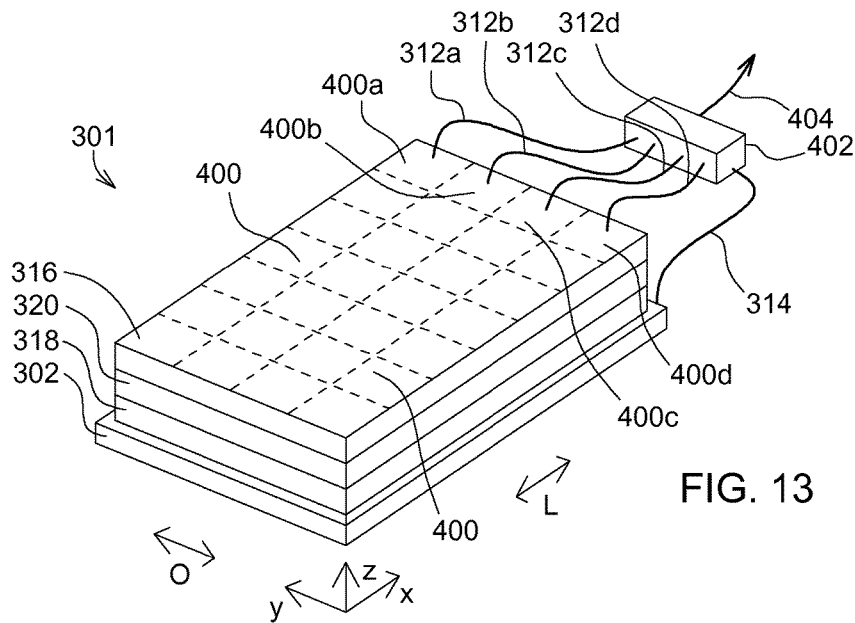

FIG. 13 shows a first alternative construction of the particulate matter impact sensor 301 in which support layer 302 similarly supports a particulate matter impact sensor 301 as described above.

In this alternative construction, however, the upper conductive layer 316 has been divided into a plurality of separate, electrically discontinuous, regions 400 (shown in FIG. 13 as 400, 400a, 400b, et seq.).

The boundaries of each of the electrically discontinuous regions (i.e. electrodes) 400 are illustrated in FIG. 13 as dashed lines. In FIG. 13, there are 28 of these regions. The regions are discontinuous in a lateral direction "L" and in a direction "0" that is orthogonal to the lateral direction "L".

The lateral direction "L" is oriented perpendicular to the direction of travel of the agricultural combine on which the particulate matter impact sensor 301 is mounted. By providing multiple regions 400 of the particulate matter impact sensor 301 that are oriented adjacent to each other in the direction "L", the particulate matter impact sensor 301 is capable of sensing the lateral distribution of seed impacts (i.e. side-to-side).

The orthogonal direction "O" is oriented parallel to the direction of travel of the agricultural combine on which the particulate matter impact sensor 301 is mounted. By providing multiple regions 400 of the particulate matter impact sensor 301 that are oriented adjacent to each other in the direction "O", the particulate matter impact sensor 301 is capable of sensing the fore-and-aft distribution of seed impacts.

Each of the regions 400 of the upper conductive layer 316 has a corresponding electrical connection 312 that is connected to a signal processing circuit 402. For convenience of illustration, only four of these electrical connections 312 are shown (312a, 312b, 312c, and 312d). The other regions 400 are similarly connected to the signal processing circuit 402.

The lower conductive layer 318 extends, unbroken, across the entire lower surface of the impact responsive layer, and thus provides a common electrical connection to the lower surface of the impact responsive layer 320 for each of the individual regions 400 (400a, 400b, etc.).

The signal processing circuit 402 is configured to receive the electrical changes (discussed above) separately from each of these regions 400 as they are generated by the impact responsive layer 320. In this manner, the electrical change generated by an impact upon the surface of the particulate matter impact sensor 301 registers on the particular corresponding upper electrical connection (312a, 312b, etc.) and on the common electrical connection 314. The signal processing circuit 402 is configured to determine the location of the impact based upon which of the electrical connections 312 (312a, 312b, etc.) generates a signal. The signal processing circuit 402 is further configured to generate an output signal on signal line 404 that indicates not only the occurrence of an impact, but also the particular region 400 (400a, 400b, etc.) of the regions 400 where the impact occurred. In this manner, the signal processing circuit 402 is configured to determine not only (i) the occurrence of an impact, but (ii) the relative (e.g. x,y or L,O) location of the impact on the particulate matter impact sensor 301.

In a second alternative arrangement similar to that of the arrangement in FIG. 13, the lower conductive layer 318 is configured as the upper conductive layer 316 is in FIG. 13, and the upper conductive layer 316 is configured as the lower conductive layer 318 is in FIG. 13. In other words, the sensing media layer 300 is reversed (compared to that in FIG. 13) such that the lower conductive layer 318 is divided into regions 400 with each region 400 having its own, separate electrical connection 314 to the signal processing circuit 402 and with a single electrical connection 314 extending across the entire top surface of the particulate matter impact sensor 301. This second alternative arrangement has the advantage of providing a substantially continuous and unbroken upper conductive layer 316, which is more resistant to repeated impacts of particles on the first surface 304 as compared to the first alternative arrangement shown in FIG. 13. Wherever there are discontinuities in the upper conductive layer 316 (such as gaps between individual regions 400) it is possible that the upper conductive layer 316 will delaminate from the impact responsive layer 320.

In a third alternative arrangement similar to that of the arrangement in FIGS. 12 and 13, both the lower conductive layer 318 and the upper conductive layer 316 are divided into regions 400. To sense electrical changes due to particulate matter impacts in a particular region 400 of the particulate matter impact sensor 301, individual electrical connections 312, 314, both upper and lower, to each region 400 are provided. Thus for each region 400, an electrical connection 312 connecting to the upper surface and electrical connection 314 connected to the lower surface of that region, and that region alone, is provided for each of the regions 400 of the particulate matter impact sensor 301 and are connected to the signal processing circuit 402.

The individual regions 400 of the upper conductive layer 316 and/or the lower conductive layer 318 for any of these three alternative arrangements can be provided in a variety of ways.

Figure 14:
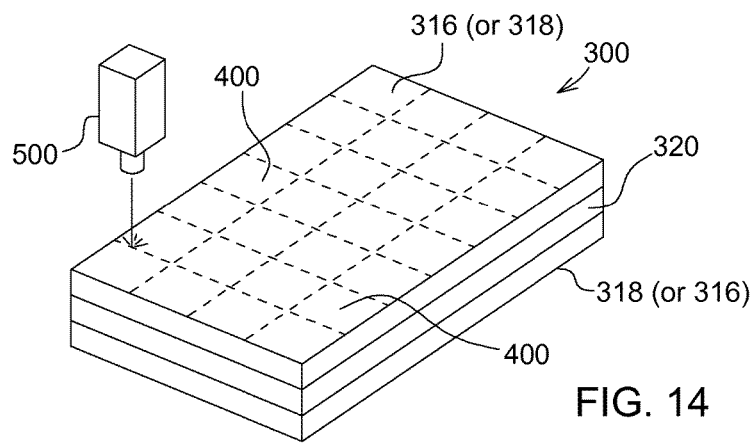

In a first process, the particulate matter impact sensor 301 can be formed as shown in FIG. 12, with a continuous upper conductive layer 316 and a continuous lower conductive layer 318 that are bonded to the impact responsive layer 320. These continuous layers can then be divided into independent regions 400 by removing the conductive material from between each adjacent region 400. This removal would follow (for example) the dashed lines shown in FIG. 12 (and shown in FIG. 13 as dashed lines 504). In this manner, the upper conductive layer 316, the lower conductive layer 318, or both of the conductive layers can be segmented into separate regions 400. This can be done, for example, by a laser 500 emitting a computer steerable laser beam 502 following the dashed lines 504 (see FIG. 14) that mark the divisions between individual regions 400.

This first process has the advantage of permitting the manufacture of a standard, uniform, and large web of material having an upper conductive layer 316, a lower conductive layer 318, and an impact responsive layer 320, and then permitting it to be cut to reduced dimensions that fit particular particulate matter impact sensor 301, then dividing either (or both) of the upper conductive layer 316 and the lower conductive layer 318 into custom regions 400 for a particular application.

In a second process, the impact responsive layer 320 can be provided, and the upper conductive layer 316 and the lower conductive layer 318 (or both) can be applied as a coating on the impact responsive layer 320 in the form of separate regions 400. This coating can be done, for example, by screen-printing of conductive materials such as conductive inks, vapor deposition of conductive material (e.g. conductive oxides such as indium tin oxide or carbon such as graphene), or plasma spray deposition of conductive material (e.g. conductive oxides or carbon).

If in the second process the coatings cannot be selectively applied as separate regions 400 to the impact responsive layer 320, then a screen, mask, or stencil can be disposed between the source of the conductive material and the impact responsive layer 320 itself during the coating process to ensure that separate regions 400 are produced on the surface of the impact responsive layer 320. In other words, that non-coated, non-conductive regions are provided (for example) where the dashed lines appear in FIG. 13 by the interposition of the screen, mask, or stencil between the source of the coating and the impact responsive layer 320.

In a third process, the upper conductive layer 316, the lower conductive layer 318, or both (depending upon the desired configuration) are provided as a continuous conductive layer on an inner surface of a film base (as described above) and then selectively removed from the film base using the first process to thereby define the regions 400. This film base (with regions 400 defined thereon) can then be fixed to the impact responsive layer 320.

In a fourth process, the upper conductive layer 316 and/or the lower conductive layer 318 can be applied as individual regions 400 on a film base (as described above) either directly or with an interposed screen, mask, or stencil. This film base (with regions 400 defined thereon) can then be fixed to the impact responsive layer 320.

Some particulate sensing environments may damage the particulate matter impact sensor 301. For example, in agricultural applications, the particulate matter impact sensor 301 may experience many thousands of seed impacts every minute, (depending upon where the particulate matter impact sensor 301 is located within an agricultural vehicle). Monocotyledon seeds 106 such as corn or maize have a sharp stalk at one end that is particularly abrasive when it impacts the particulate matter impact sensor 301.

To prevent excessive damage to the particulate matter impact sensor 301 it is beneficial to provide one or more protective layers 600 to cover the upper conductive layer 316. One arrangement of the particulate matter impact sensor 301 with a protective layer 600 is shown in FIG. 15 and FIG. 16. The protective layer 600 is fixed to the particulate matter impact sensor 301. The protective layer 600 substantially covers the upper conductive layer 316, thereby protecting it against wear and erosion. When impacted by particulate matter such as seeds, the protective layer 600 deforms (i.e. flexes inward), bending the upper conductive layer 316 underneath it, which in turn deforms the impact responsive layer 320 and compresses the impact responsive layer 320 against the lower conductive layer and the support layer 302.

In one arrangement the protective layer 600 comprises a plastic laminate. The plastic laminate may comprise a fiber reinforced plastic. The fiber reinforced plastic may comprise a glass fiber reinforced plastic or a carbon fiber reinforced plastic. The glass fiber reinforced plastic may comprise a chopped fiber and resin laminate or it may comprise a woven fiber cloth embedded in an epoxy resin binder. The woven fiber cloth that is embedded in an epoxy resin binder may comprise National Electrical Manufacturer Association (NEMA) FR-4 grade material or NEMA G-10 grade material. The thickness of the protective layer 600 is in the range of 0.1 to 1.0 mm when using FR-4 grade or G-10 grade material.

In another arrangement, the protective layer 600 comprises plastic. The plastic may comprise a polyester material. The plastic may comprise polyethylene terephthalate (PET).

In another arrangement, the protective layer 600 comprises a metal. The metal may comprise a light metal, e.g. aluminum or an aluminum alloy, or a heavier metal, e.g. steel.

The protective layer, when made from G-10 or FR-4, has a thickness of 0.1 to 1.0 mm. Alternatively it has a thickness 0.15 to 0.8 mm. Alternatively it has a thickness of 0.2 to 0.6 mm. When made of other materials, the protective layer 600 has a thickness sufficient to provide an equivalent flexural rigidity as the flexural rigidity of the protective layer of G-10 or FR-4 with the stated thickness ranges.

The protective layer 600 is fixed to the particulate matter impact sensor 301 with an adhesive layer 602 that is disposed between the protective layer 600 and the upper conductive layer 316.

This document describes several examples of ways to construct and use the invention. These examples do not define or limit the invention. They are merely illustrations of several ways in which to create and use devices that are covered by the claims. The invention is defined by the claims below. Other ways of creating a device that falls within the scope of the claims will be apparent to one skilled in the art.

The invention claimed is:

1. A particulate matter impact sensor for sensing impacts of particles comprises:
   a support layer; and
   a sensing media layer disposed in front of the support layer, the sensing media layer comprising internal elliptical voids.

2. The particulate matter impact sensor according to claim 1, wherein the sensing media layer comprises an impact responsive layer having an outer surface facing a direction of material flow and an inner surface facing the support layer.

3. The particulate matter impact sensor according to claim 1, wherein the sensing media layer has a thickness of no greater than 500 .mu.m.

4. The particulate matter impact sensor according to claim 1, wherein the sensing media layer is comprised of biaxially stretched polypropylene.

5. The particulate matter impact sensor according to claim 1, further comprising a protective layer that is fixed to the sensing media layer and is located between the particles impacting the particulate matter impact sensor and the sensing media layer.

6. The particulate matter impact sensor according to claim 5, wherein the protective layer comprises plastic or metal.

7. The particulate matter impact sensor according to claim 6, wherein the protective layer comprises a plastic laminate.

8. The particulate matter impact sensor according to claim 7, wherein the plastic laminate comprises a fiber reinforced plastic.

9. The particulate matter impact sensor according to claim 8, wherein the fiber reinforced plastic comprises glass fibers or carbon fibers.

10. The particulate matter impact sensor according to claim 6, wherein the protective layer comprises aluminum.

11. The particulate matter impact sensor according to claim 1 further comprising:
    a first conductive layer; and
    a second conductive layer, wherein the sensing media layer is sandwiched between the first conductive layer and the second conductive layer.

12. The particulate matter impact sensor according to claim 11, wherein the first conductive layer and the second conductive layer are segmented into separate regions.

13. The particulate matter impact sensor according to claim 12, wherein the separate regions comprise an array of at least three regions by three regions.

14. The particulate matter impact sensor according to claim 11, wherein each of the regions has an associated electrical connection distinct from electrical connections of other ones of the regions.

15. The particulate matter impact sensor according to claim 14 further comprising a signal processing circuit configured to determine an occurrence of an impact and which of the regions experienced the occurrence of the impact.

16. The particulate matter impact sensor according to claim 14, wherein adjacent regions are spaced from one another.

17. The particulate matter impact sensor according to claim 1, wherein the elliptical voids have major axes that extend parallel to support layer.

18. The particulate matter impact sensor according to claim 1, wherein all of the elliptical voids have major axes extending parallel to the support layer.

19. A particulate matter impact sensor for sensing impacts of particles comprises:
    a support layer; and
    a sensing media layer disposed in front of the support layer, the sensing media layer comprising a layer of material encapsulating internal elliptical voids, wherein the material forms an entirety of an inner surface of each of the voids.

20. A particulate matter impact sensor for sensing impacts of particles comprises:
    a support layer; and
    a sensing media layer having a first surface (304) that faces a direction of flow of grain particles and a second surface on the opposite side of the sensing media layer bonded to a first surface of the support layer; and
    a protective layer that is fixed to the sensing media layer and located between the grain particles impacting the particulate matter impact sensor and the sensing media layer,
    wherein the sensing media layer comprises an impact responsive layer comprising a pressure sensitive media adapted to change its electrical characteristics upon the impact of a grain particle traveling in the direction of flow of grain particles and to produce an electrical signal at one or more electrical connections electrically coupled to the sensing media layer,
    wherein the sensing media layer further has an upper conductive layer on its first surface, the upper conductive layer coupled to one of the electrical connections and a lower conductive layer on its second surface, the lower conductive layer coupled to another one of the electrical connections, and
    wherein the protective layer is a flexible film layer and that the lower conductive layer and the upper conductive layer each comprise a film base to which a conductive media is deposited by a sputter-, vapor- or plasma deposition process.

* * * * *